United States Patent [19]

Skinner et al.

[11] 4,156,664

[45] May 29, 1979

[54] FILM FORMING SGP

[75] Inventors: Earl L. Skinner, Wayzata; Lyle F. Elmquist, North St. Paul, both of Minn.

[73] Assignee: Henkel Corporation, Minneapolis, Minn.

[21] Appl. No.: 873,986

[22] Filed: Jan. 31, 1978

[51] Int. Cl.$^2$ .............................................. C08L 3/02
[52] U.S. Cl. ...................... 260/17.4 GC; 260/17.4 ST
[58] Field of Search ................................ 260/17.4 GC

[56] References Cited

U.S. PATENT DOCUMENTS

| | | | |
|---|---|---|---|
| 3,485,777 | 12/1969 | Gaylord | 260/17.4 |
| 3,935,099 | 1/1976 | Weaver et al. | 210/43 |

*Primary Examiner*—Edward M. Woodberry
*Attorney, Agent, or Firm*—Patrick J. Span; Elizabeth Tweedy

[57] ABSTRACT

Film forming starch-hydrolyzed polyacrylonitrile graft copolymer and latex composition.

2 Claims, No Drawings

FILM FORMING SGP

This invention relates to absorbent film forming compositions. More particularly, this invention relates to combinations of starch-hydrolyzed polyacrylonitrile graft copolymer and a latex selected from nonionic or anionic latices. When dried from aqueous dispersions, this combination forms films which adhere to fabrics or other substrates while retaining the absorbency of the starch-hydrolyzed polyacrylonitrile graft copolymer.

BACKGROUND OF THE INVENTION

Starch-hydrolyzed polyacrylonitrile graft copolymers exhibiting the capacity to absorb from about 300 to 1000 times their weight of deionized water are known at this time. The development of these compositions was carried out by the Northern Regional Research Laboratory, Peoria, Ill. The starch-hydrolyzed polyacrylonitrile graft copolymer is produced by exposure of starch, either gelatinized or ungelatinized, to a catalyst such as ceric ammonium nitrate which acts as a catalyst to generate free radicals in the starch chain. Polyacrylonitrile chains become attached to these free radicals by copolymerization. A wide range of substitution in these copolymers is known in the art. For example, U.S. Pat. No. 3,035,099 shows the preparation of copolymers in which the starch to polyacrylonitriles molar ratios range from 1:1.5 to 1:9. The variations in molar ratio of the components of the copolymer is not critical to the practice of this invention. The resulting material is then saponified in sodium hydroxide to hydrolyze the polyacrylonitrile chains to carboxy amide and alkali metal carboxylate groups mixed with metal salts. Drying the hydrolyzed material can be accomplished by tumble air drying or vacuum drying. After drying, the material can absorb about 300 to 400 times it weight. Washing the copolymer before drying with alcohol increases its absorbency to 800 to 1000 times its weight.

The copolymer can be made as film, flakes, powder or mat. These forms take up water, swelling but not dissolving and hold it in expanded duplications of their own dry shapes. Films extend and thicken in all dimensions. Powders become piles of water textured like crushed ice. A flake expands to a clear, angular piece of water. The swollen forms shrink in dilute acid, expand again in dilute alkali solution. They also shrink as they dry and expand again when absorbing water.

The copolymer, with these properties, can be mixed with or coated on a wide variety of materials including, for example, sand, straw, sawdust, seeds and roots, natural or synthetic fibers, flour, gelatin, and starch. It can hold water in soils, animal bedding and kitty litter, toweling and diapers, bandages, surgical pads, and dental absorbents.

Some of the major problems in using the copolymer is that the dry copolymer films are extremely brittle and adhere poorly to substrates. The copolymer in powder form is difficult to hold in position.

SUMMARY OF THE INVENTION

It has now been found that from aqueous dispersions of starch-hydrolyzed polyacrylonitrile graft copolymers and an anionic or non-ionic latex, films can be cast which vary in handleability from flexible to brittle. In addition these films readily adhere to substrates such as fabrics.

The composition useful in making absorbent adhesive film comprises about 2 to 98% by weight starch-hydrolyzed polyacrylonitrile graft copolymer and about 2 to 98% by weight acrylic, styrene, vinyl, or butadiene type latex. The components are dispersed in water. The amount of water is not critical inasmuch as it is a suspending vehicle and during drying evaporates away from the resulting film.

DETAILS OF THE INVENTION

By the term latex is meant a heterogeneous fluid composed of small globules or particles of natural or synthetic rubber or plastic suspended in a continuous aqueous phase. The anionic or non-ionic character of latices is determined by the anionic or non-ionic nature of the emulsifier used to maintain the globules or particles in suspension. Examples of anionic emulsifiers are sodium alkyl ether sulphate, sodium salt of alkylauryl polyether sulfonate, sodium salt of alkylauryl polyether sulfate, phosphate surfactant potassium salt, dioctyl sodium sulfosuccinate, sodium high ethoxy ether sulfate, and sodium lauryl sulfate.

Examples of non-ionic emulsifiers include a series of compounds formed by addition of propylene oxide to an alcohol, followed by the addition of ethylene oxide. Examples of the results are polyethylene glycol ether of linear alcohol, nonylphenol polyethylene glycol ether, and octyl-phenoxy polyethoxy ethanol.

Examples of monomers commonly polymerized to form polymers suspended in latices are styrene, methyl methacrylate, butylacrylate, acrylic acid, vinyl acetate, dibutyl maleate, combinations of stearic acid and butadiene, stearic acid and acrylic acid. The latices may be the self cross-linking type, the type to which a cross-linker is added, or a noncross-linking type. Useful latices are those having glass transition points between about 20° F. to 110° F.

The blend of starch-hydrolyzed polyacrylonitrile graft copolymer and the latex can be obtained by mixing the components together. The starch-hydrolyzed polyacrylonitrile graft copolymer can be placed in a blender with about 20 to 40 times its weight of water and mixed until the copolymer is dispersed in the water and the dispersion has a smooth appearance. The latex can then be added slowly and mixing continued. Generally a homogenous white color indicates the dispersion is sufficiently uniform for the purposes of making absorptive films. The dispersion is then spread onto a surface such as paper, plastic, or fiber and dried. Drying can be conducted at temperatures from about 10° C. to 110° C. for a period of about 10 minutes to several days. The dried film or coating exhibits greater absorbency than films of starch-hydrolyzed polyacrylonitrile graft copolymer alone.

The handleability of the final films varies from very flexible to brittle depending upon the glass transition point of the latex used. For example, acylic latices having the following compositions:

| Sample No. | Parts by Weight | | |
|---|---|---|---|
| | I | II | III |
| Deionized Water | 57.17 | 57.17 | 57.17 |
| Sodium alkyl ether sulphate anionic | | | |

-continued

| Sample No. | Parts by Weight | | |
|---|---|---|---|
| | I | II | III |
| liquid, 25% conc. | 3.05 | 3.05 | 3.05 |
| Lauryl mercaptan (chain transfer agent) | 1.15 | 1.15 | 1.15 |
| Ammonium persulfate (polymerization catalyst) | 0.19 | 0.19 | 0.19 |
| Ethyl acrylate | 20.83 | 13.85 | 6.94 |
| Methyl methacrylate | 13.85 | 20.83 | 27.74 |
| Acrylic acid | 3.51 | 3.51 | 3.51 |
| Formalin (Activator for catalyst) | 0.25 | 0.25 | 0.25 |
| Glass transition point (tg) | 18° C. (64° F.) | 40° C. (104° F.) | 0° C. (32° F.) | display the following properties. Sample I which is also shown in Example II produces a brittle film when incorporated with starch-hydrolyzed polyacrylonitrile graft copolymer. Sample II produces a very hard and brittle film with the copolymer. Sample III produces a soft film with the copolymer. Conversely the acrylic copolymer latex sold under the tradename Rhoplex AC-388 ® by Rohm and Haas Company, believed to contain methyl methacrylate, butyl acrylate and acrylic acid, produces a flexible film as shown in Example I.

The films shown below in Examples I through IV all adhered to the substrate when cast on fabric. In addition, the films when submerged in water absorbed approximately the same amount of water as the starch-hydrolyzed polyacrylonitrile graft copolymer component absorbed alone.

EXAMPLE I

Starch-hydrolyzed polyacrylonitrile graft copolymer in an amount of 8.333 g. on an as is basis was dispersed in about 250 ml. water by mixing in a blender until smooth. To this was slowly added 8.334 g. of nonionic acrylic latex, sold under the tradename Rhoplex AC-388 ® by Rohm and Haas. Mixing was continued during and after the addition of the acrylic emulsion until the blend had a homogeneous white color. The mixture was spread in a 50 mil film on a tetrafluoroethylene cloth using a Boston Bradley Adjustable Blade.

One portion of the film was dried for three hours at a temperature of 100° F. and another portion was dried for four days. Both portions were flexible and appeared to be very much alike. Both portions could be rolled up and placed in a sample bottle. The films appeared to hydrate and swell rapidly in deionized water. They were both cloudy in appearance.

EXAMPLE II

Following the procedure of Example I, anionic latex shown on page 4 of the specification was combined with starch-hydrolyzed polyacrylonitrile graft copolymer. The film appeared flexible before completely dry but overnight became brittle and broke up when placed in a sample bottle.

EXAMPLE III

Following the procedure set out in Example I, a film was made from starch-hydrolyzed polyacrylonitrile graft copolymer and an acrylic emulsion slurry sold under the tradename HA-8 by Rohm and Haas Co. Starch-hydrolyzed polyacrylonitrile graft copolymer in an amount of 8.333 grams on an as is basis were slurried in 250 ml. of deionized water in a one quart blender. To the slurry was added 9.17 g. of the acrylic emulsion. A free film was cast on tetrafluoroethylene sheeting with a spreader bar with an 0.05 inch nip. The film was dried overnight at a temperature of 100° F. The dried film was flexible enough to roll up with some cracking.

EXAMPLE IV

Following the procedure of Example I, two films were made using two different acrylic latices: Rhoplex B-5 ® and Rhoplex B-15 ® sold under those tradenames by Rohm and Haas Co.

The ingredients used are listed below:

| Components | Sample 1 | Sample 2 |
|---|---|---|
| Water | 250 ml. | 250 ml. |
| Rhoplex B-15 ® solids | 4.17 gm. | |
| Rhoplex B-5 ® solids | | 4.17 gm. |
| Graft Copolymer | 8.33 gm. | 8.33 gm. |

The starch-hydrolyzed polyacrylonitrile graft copolymer was mixed in 250 ml. of deionized water in a one quart blender. Care was taken to maintain minimum aeration. The acrylic latex was added and mixing was continued. The respective films were then cast on tetrafluoroethylene sheets with an 0.05 inch draw down bar. The films were dried overnight at a temperature of 100° F.

The embodiments of the invention in which an exclusive property or privilege is claimed are defined as follows:

1. A combination of starch-hydrolyzed polyacrylonitrile graft copolymer and a latex comprising about 2 to 98% by weight starch-hydrolyzed polyacrylonitrile graft copolymer and about 2 to 98% by weight of a latex selected from anionic and nonionic latices having glass transition points between about 20° F. and 110° F.

2. The combination of claim 1 in which the latex is an acrylic latex.

* * * * *